(12) United States Patent
Gazit et al.

(10) Patent No.: US 11,142,496 B2
(45) Date of Patent: Oct. 12, 2021

(54) METHOD FOR SYNTHESIS OF 9-CIS-BETA-CAROTENE AND FORMULATIONS THEREOF

(71) Applicant: Ramot at Tel-Aviv University Ltd., Tel Aviv (IL)

(72) Inventors: Ehud Gazit, Ramat-Hasharon (IL); Ludmila Buzhansky, Ariel (IL); Michael Ioffe, Holon (IL); Alon Sayer, Holon (IL)

(73) Assignee: Ramot at Tel-Aviv University Ltd., Tel Aviv (IL)

( * ) Notice: Subject to any disclaimer, the term of this patent is extended or adjusted under 35 U.S.C. 154(b) by 270 days.

(21) Appl. No.: 16/303,604

(22) PCT Filed: May 21, 2017

(86) PCT No.: PCT/IL2017/050565
§ 371 (c)(1),
(2) Date: Nov. 20, 2018

(87) PCT Pub. No.: WO2017/203516
PCT Pub. Date: Nov. 30, 2017

(65) Prior Publication Data
US 2019/0367451 A1  Dec. 5, 2019

(30) Foreign Application Priority Data
May 25, 2016 (IL) .......................................... 245847

(51) Int. Cl.
| | | |
|---|---|---|
| *C07C 403/24* | (2006.01) |
| *C07C 45/60* | (2006.01) |
| *C07C 67/00* | (2006.01) |
| *A61K 9/00* | (2006.01) |
| *A61K 31/015* | (2006.01) |
| *A61K 47/10* | (2017.01) |
| *A61K 47/14* | (2017.01) |
| *A61K 47/24* | (2006.01) |
| *A61K 47/44* | (2017.01) |
| *C07C 67/44* | (2006.01) |
| *C07C 403/02* | (2006.01) |
| *C07C 403/00* | (2006.01) |

(52) U.S. Cl.
CPC .......... *C07C 403/24* (2013.01); *A61K 9/0053* (2013.01); *A61K 31/015* (2013.01); *A61K 47/10* (2013.01); *A61K 47/14* (2013.01); *A61K 47/24* (2013.01); *A61K 47/44* (2013.01); *C07C 45/60* (2013.01); *C07C 67/44* (2013.01); *C07C 403/00* (2013.01); *C07C 403/02* (2013.01); *C07C 2601/16* (2017.05)

(58) Field of Classification Search
CPC ........ C07C 403/24; C07C 45/60; C07C 67/44
See application file for complete search history.

(56) References Cited

U.S. PATENT DOCUMENTS

| 5,567,855 A | 10/1996 | White et al. |
| 5,612,485 A | 3/1997 | Schlipalius |

OTHER PUBLICATIONS

International Preliminary Report on Patentability received in PCT Application No. PCT/IL2017/050565, dated Nov. 27, 2018.
Bennani, Youssef L.; Boehm, Marcus F. "Syntheses of High Specific Activity 2, 3-and 3, 4-[3H] 2-9-cis-Retinoic Acid" The Journal of Organic Chemistry, 1, 60.5: pp. 1195-1200. (1995).
Alvarez, Rosana; Dominguez, Beatriz; De Lera, Angel R. "An expedient stereocontrolled synthesis of 7-cis-retinoids" Synthetic Communications, 31.13: pp. 2083-2087. (2001).
Goswami, Bhabesh C.; Barua, Arun B. "Synthesis of tracer labelled [11, 12-3H]-beta-carotene". Journal of Labelled Compounds and Radiopharmaceuticals, 46.9: pp. 843-849. (2003).
Alvarez, R.; Dominguez, M.; Pazos, Y.; Sussman, F.; de Lera, A.R.,"(9Z)- and (11Z)-8-Methylretinals for Artificial Visual Pigment Studies: Stereoselective Synthesis, Structure, and Binding Models" Chem. Eur. J. , 9, pp. 5821-5831.
López, S.; Montenegro, J.; Saá, C., "Highly Convergent, Stereospecific Synthesis of 11-cis-Retinoids by Metal-Catalyzed Cross-Coupling Reactions of (Z)-1-Alkenylmetals" J. Org. Chem. 72, pp. 9572-9581. (2007).
Mata, E.G.; Thomas, E.J., "Development of a synthesis of lankacidins: an investigation into 17-membered ring formation" J. Chem. Soc.-Perkin Trans. 1 , pp. 785-799. (1995).
Roder, E.; Wiedenfeld, H.; Frisse, M., ."Zur Synthese der 5-Hydroxy-2,4-dimethyl-l-hexen-I,5- dicarbonsaure (Nemorensinsaure)" Arch Pharm. , 313, pp. 803-806. (1980).
International Search Report and Written Opinion dated Jul. 18, 2017 for PCT/IL2017/050565.

*Primary Examiner* — Sikarl A Witherspoon
(74) *Attorney, Agent, or Firm* — Knobbe, Martens, Olson & Bear, LLP

(57) ABSTRACT

The present invention relates to a method for total chemical synthesis of 9-cis-β-carotene (9CBC), and further provides stable formulations thereof.

4 Claims, 1 Drawing Sheet

METHOD FOR SYNTHESIS OF 9-CIS-BETA-CAROTENE AND FORMULATIONS THEREOF

TECHNICAL FIELD

The present invention relates to a method for total chemical synthesis of 9-cis-β-carotene (9CBC) and to stable formulations thereof.

BACKGROUND ART

Neuro-retinal degeneration including age related macular degeneration (AMD) and retinitis pigmentosa (RP) are the leading cause of vision incapacitation and blindness worldwide. Such indications might be effectively treated using 9CBC.

9CBC is currently obtained by isolation from a β-carotenes mixture derived from *Dunaliella bardawil* algae. The β-carotene mixture derived from said algae contains about 50% of the 9-cis isomer; however, the exact amount of said isomer varies depending on inter alia the season, light irradiation, and temperature. Isolation of the 9-cis isomer from the carotenes mixture requires an extraction process that is followed by HPLC reverse phase separation phase. The product is currently available from several commercial sources; however, due to the complex process involved, it is highly expensive.

No total synthesis of 9CBC has been reported by the date; however, extensive efforts have been made so as to develop a stereo-controlled total synthesis of this compound. The strategies developed for the polyenic chain construction were based on the Wittig, Horner-Wadsworth-Emmons and related reactions; however, in all cases, mixtures of E/Z isomers were obtained and the separation of the specific isomer was quite difficult (US Patent Publication No. 20060183185).

SUMMARY OF INVENTION

In one aspect, the present invention relates to a convenient and cost-effective synthetic route for the preparation of 9CBC or derivatives thereof, which are known to have therapeutic effects in, e.g., neuro-retinal degeneration. More particularly, the invention relates to a method for the synthesis of 9CBC or a derivative thereof, starting from 4-methyl-6-(2,6,6-trimethylcyclohex-1-en-1-yl)-5,6-dihydro-2H-pyran-2-one, which may be synthesized from β-cyclocitral, e.g., by Reformatsky reaction of said β-cyclocitral with a compound such as ethyl 4-bromo-3-methylbut-2-enoate.

The starting materials, intermediates, and final product mentioned in connection with the synthetic process of the present invention are herein identified by the Arabic numbers 1-9 in bold, and are shown in Scheme 1 illustrating the particular synthetic route exemplified. β-Cyclocitral is identified as compound 1; the lactone 4-methyl-6-(2,6,6-trimethylcyclohex-1-en-1-yl)-5,6-dihydro-2H-pyran-2-one and the corresponding lactol 4-methyl-6-(2,6,6-trimethylcyclohex-1-en-1-yl)-5,6-dihydro-2H-pyran-2-ol are identified as compounds 3 and 4, respectively; and 9CBC is identified as compound 9.

More specifically, the invention relates to a method for the synthesis of 9CBC or a derivative thereof, said method comprising:

(i) reducing the lactone 4-methyl-6-(2,6,6-trimethylcyclohex-1-en-1-yl)-5,6-dihydro-2H-pyran-2-one (compound 3) and opening the ring of the lactol obtained (compound 4) with complete retention of the double bond configuration, to thereby obtain (2Z,4E)-3-methyl-5-(2,6,6-trimethyl cyclohex-1-en-1-yl)penta-2,4-dienal (compound 5);

(ii) subjecting the (2Z,4E)-3-methyl-5-(2,6,6-trimethylcyclohex-1-en-1-yl) penta-2,4-dienal to Horner-Emmons reaction to obtain a 9-cis retinyl ester (compound 6);

(iii) reducing the 9-cis retinyl ester to obtain 9-cis retinol, i.e., vitamin A (compound 7); and (iv) converting the 9-cis retinol to its triphenylphosphonium salt (compound 8), and subjecting said triphenylphosphonium salt to Wittig reaction with a compound of the formula A:

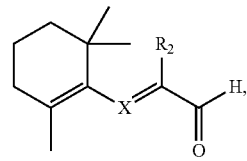

wherein $R_2$ is H or methyl; X is

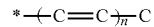

optionally substituted with one or more methyl groups; n is an integer of 0-16; and the asterisk represents the point of attachment to the cyclohexene ring, in the presence of a strong base, to thereby obtain said 9CBC or derivative thereof.

In a particular embodiment, the triphenylphosphonium salt of 9-cis retinol is subjected, in step (iv), to Wittig reaction with all-trans retinal (representing a compound of the formula A) to obtain 9CBC.

The 4-methyl-6-(2,6,6-trimethylcyclohex-1-en-1-yl)-5,6-dihydro-2H-pyran-2-one (compound 3) used as a starting material in the method of the invention may be synthesized by any suitable process. In particular embodiments, compound 3 is prepared from β-cyclocitral (compound 1), by reacting with a compound of the formula B:

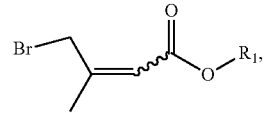

wherein $R_1$ is $(C_1-C_8)$alkyl or $(C_6-C_{10})$aryl, in the presence of metallic zinc (Zn), in a Reformatsky reaction.

In another aspect, the present invention relates to 9CBC or a derivative thereof, synthesized by the method disclosed herein, wherein said derivative is of the formula C:

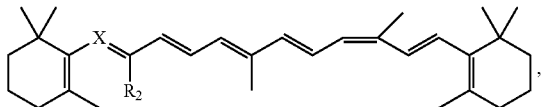

wherein $R_2$ is H or methyl; X is

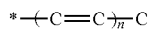

optionally substituted with one or more methyl groups; n is an integer of 0-16; and the asterisk represents the point of attachment to the cyclohexene ring.

Initial stability tests indicated that synthetic 9CBC is sensitive to both oxygen and UV degradation due to the highly conjugated nature of the carbon chain, resulting in full decomposition in less than 24 hours. Attempt to stabilize 9CBC by the addition of antioxidant(s), as suggested in the prior art, were unsuccessful, as such a composition has quite rapidly degraded. As has been surprisingly found and shown herein, a 9CBC formulation comprising, as non-active ingredients, a viscosity enhancing agent such as a lecithin, e.g., a soybean lecithin, a medium chain triglyceride such as miglyol, or a polysorbate such as polysorbate 20 and polysorbate 40; as well as one or more antioxidants, are highly stable for a long period of time.

In a further aspect, the present invention thus provides a formulation, more particularly a pharmaceutical formulation/composition, comprising an active agent selected from 9CBC or a derivative thereof of the formula C as defined above, a thickening- or solidifying-, i.e., viscosity enhancing, agent, and an antioxidant. Such pharmaceutical formulations are useful for treatment of any medical indication in which administration of 9CBC or a derivative thereof as defined above is useful, e.g., neuro-retinal degeneration.

DETAILED DESCRIPTION

Figure 1:
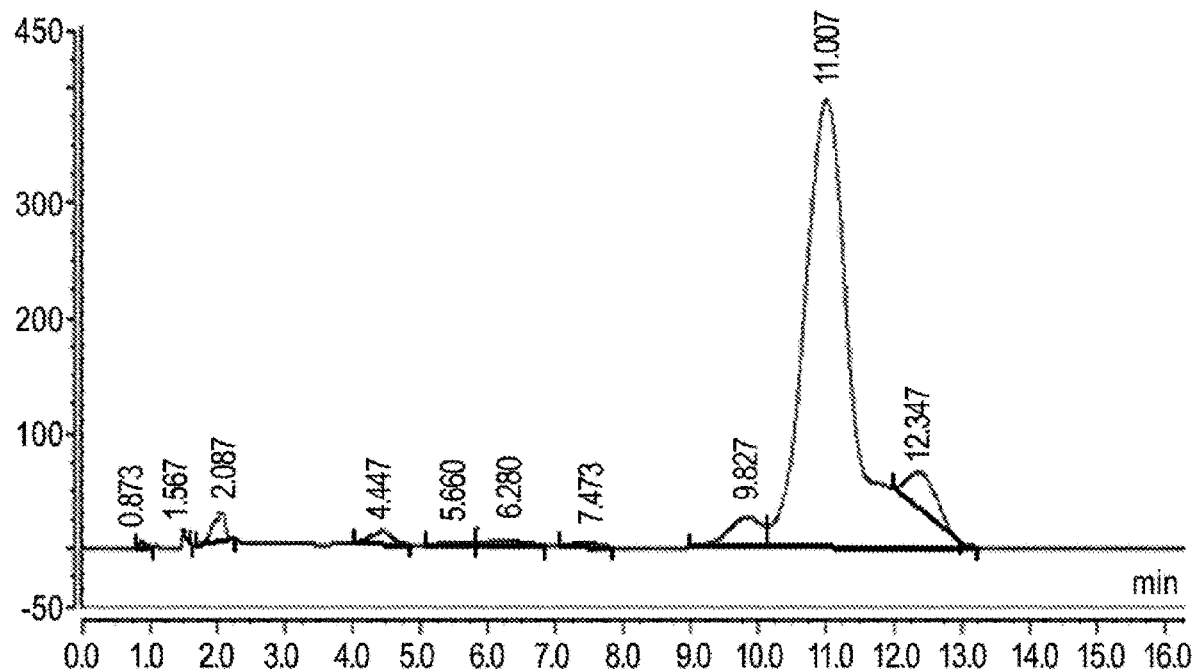
FIG. 1 shows HPLC reversed phase analysis of 9CBC reaction mixture ($\lambda$=447 nm).
Figure 2:
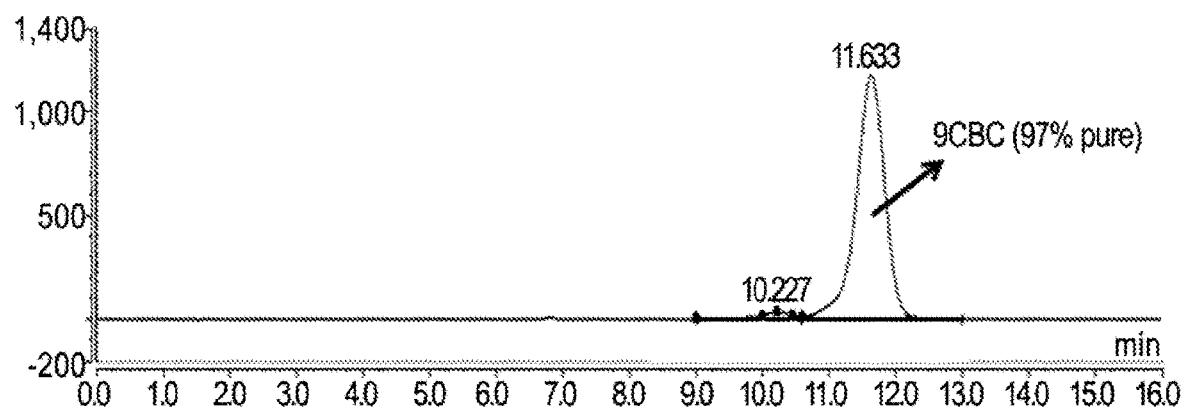
FIG. 2 shows HPLC analysis ($\lambda$=447 nm) of purified 9CBC (2 mL of 8:2 $CH_3OH$:$CHCl_3$) with 1 μL DMSO.

As shown herein, a multi-steps process for the synthesis of 9CBC from common available compounds was developed based on stereospecific synthesis of 9-cis olefin intermediate via a lactone ring opening with complete retention of double bond configuration, followed by Horner-Emmons, ester reduction and Witting reaction to produce the final compound.

In one aspect, the present invention relates to a method for the synthesis of 9CBC or a derivative thereof, as defined above, i.e., starting from the lactone 4-methyl-6-(2,6,6-trimethylcyclohex-1-en-1-yl)-5,6-dihydro-2H-pyran-2-one (compound 3).

The term "alkyl" as used herein typically means a linear or branched saturated hydrocarbon radical having 1-8 carbon atoms and includes, e.g., methyl, ethyl, n-propyl, isopropyl, n-butyl, sec-butyl, isobutyl, tert-butyl, n-pentyl, isoamyl, 2,2-dimethylpropyl, n-hexyl, n-heptyl, n-octyl, and the like. Preferred are ($C_1$-$C_6$)alkyl groups, more preferably ($C_1$-$C_4$)alkyl groups, most preferably methyl, ethyl, propyl or isopropyl. The alkyl may optionally be substituted with one or more groups each independently selected from halogen, —COR, —COOR, —CN, —$NO_2$, —SR, —OR, —N(R)$_2$, —CON(R)$_2$, —$SO_2$R, —$SO_3$R or —S(=O)R, wherein R is H or unsubstituted linear or branched ($C_1$-$C_8$) alkyl.

The term "aryl" as used herein denotes an aromatic carbocyclic group having 6-10 carbon atoms consisting of a single ring or condensed multiple rings such as, but not limited to, phenyl and naphthyl. The aryl may optionally be substituted with one or more groups each independently selected from halogen, —COR, —COOR, —CN, —$NO_2$, —SR, —OR, —N(R)$_2$, —CON(R)$_2$, —$SO_2$R, —$SO_3$R, —S(=O)R, or —($C_1$-$C_8$)alkyl, wherein R is H or unsubstituted linear or branched ($C_1$-$C_8$)alkyl.

The term "halogen" as used herein includes fluoro, chloro, bromo, and iodo, but it is preferably fluoro, chloro or bromo.

In certain embodiments, the reduction in step (i) of the method of the invention is carried out with diisobutylaluminum hydride (DIBAL-H).

In certain embodiments, opening the ring of the lactol in step (i) of the method of the invention is carried out in the presence of a strong acid. Non-limiting examples of suitable acids include HCl, $HClO_4$, $HClO_3$, $HNO_3$, HBr, HI, and $H_2SO_4$. In a particular embodiment, opening the ring of the lactol in step (i) is carried out in the presence of HCl.

In certain embodiments, the Horner-Emmons reaction in step (ii) of the method of the invention is carried out with triethyl 3-methyl-4-phosphono-2-butenoate to obtain 9-cis retinyl ethyl ester.

In certain embodiments, converting the 9-cis retinol to its triphenylphosphonium salt in step (iv) of the method of the invention is carried out with triphenylphosphine.

In certain embodiments, the triphenylphosphonium salt of 9-cis retinol is subjected, in step (iv) of the method of the invention, to Wittig reaction with all-trans retinal, representing the compound of the formula A, to obtain 9CBC.

4-methyl-6-(2,6,6-trimethylcyclohex-1-en-1-yl)-5,6-dihydro-2H-pyran-2-one for use as a starting material in step (i) of the method of the invention may be synthesized by any suitable process. In certain embodiments, this lactone is synthesized from β-cyclocitral (compound 1), by reacting β-cyclocitral with a compound of the formula B:

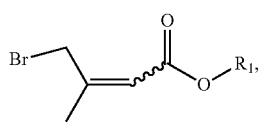

wherein $R_1$ is ($C_1$-$C_8$)alkyl or ($C_6$-$C_{10}$)aryl, in the presence of metallic Zn, in a Reformatsky reaction. In a particular such embodiment exemplified herein, 4-methyl-6-(2,6,6-trimethylcyclohex-1-en-1-yl)-5,6-dihydro-2H-pyran-2-one is obtained by reacting β-cyclocitral with a compound of the formula B wherein $R_1$ is ethyl, i.e., with ethyl 4-bromo-3-methylbut-2-enoate (compound 2).

In another aspect, the present invention relates to 9CBC or a derivative thereof, synthesized by the method disclosed herein, wherein said derivative is of the formula C:

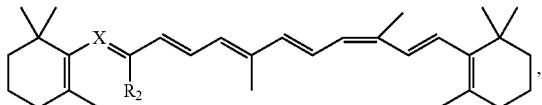

wherein $R_2$ is H or methyl; X is

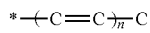

optionally substituted with one or more methyl groups; and n is an integer of 0-16; and the asterisk represents the point of attachment to the cyclohexene ring. The 9CBC or derivative thereof prepared by the method of the present invention may be crude or purified to a certain level if necessary, and may thus contain varying amounts of impurities left from the synthetic procedure as disclosed herein, i.e., traces of one or more of the intermediates formed, or reagents added, during the procedure.

In a further aspect, the present invention provides a formulation comprising an active agent, a thickening/solidifying, i.e., viscosity enhancing, agent, and at least one (i.e., one or more) antioxidant, wherein said active agent is 9CBC or a derivative thereof of the formula C as defined above. Particular such formulations may further comprise a pharmaceutically acceptable carrier, and are thus referred to herein as pharmaceutical formulations or pharmaceutical compositions.

The term "thickening agent", "solidifying agent", or "viscosity enhancing agent", used herein interchangeably, means an agent that is solid or semi-solid in the dry form, i.e., when not dissolved in a liquid medium, capable of increasing the viscosity of a liquid without substantially changing its other physico-chemical properties, and has a fair solubility in non-polar organic solvents such as pentane, cyclopentane, hexane, cyclohexane, benzene, toluene, 1,4-dioxane, chloroform, diethyl ether, and dichloromethane; polar organic solvents such as formic acid, n-butanol, tert-butanol, isopropanol, n-propanol, ethanol, methanol, acetic acid, and dimethyl sulfoxide (DMSO); water; or buffer solutions.

In certain embodiments, the thickening/solidifying agent comprised within the formulation of the present invention comprises a lecithin or a PEGylated derivative thereof; a lecithin-like substance; a medium chain triglyceride or a mixture thereof; a povidone, also referred to as polyvidone or polyvinylpyrrolidone (linear formula: $[C_6H_9NO]_n$, CAS: 9003-3908); a polysorbate; or sorbitol.

In certain particular such embodiments, said thickening/solidifying agent comprises a lecithin or a PEGylated derivative thereof, a lecithin-based product, or a povidone. More particular such embodiments are those wherein the viscosity enhancing agent comprises egg lecithin, soybean lecithin, or a PEGylated derivative thereof; or those wherein the viscosity enhancing agents comprises a lecithin-based product such as L-α-lecithin, granular (Acros Organics™, Fisher Scientific), which is a soybean lecithin concentrate consisting of more than 94% phosphatidylcholine and less than 2% triglycerides; CAS: 8002-43-5) (https://www.fishersci.com/shop/products/1-alpha-lecithin-granular-acros-organics-2/p-153301; Phospholipon® 50, Phospholipon® 75, Phospholipon® 85G or Phospholipon® 90G, essentially consisting of soybean lecithin and phospholipids; Phospholipon® 80H or Phospholipon® 90H, essentially consisting of hydrogenated soybean lecithin and phospholipids; Phospholipon® E25, Phospholipon® E35 or Phospholipon® E, essentially consisting of egg yolk lecithin and phospholipids; and Phospholipon® LPC20, Phospholipon® LPC25 or Phospholipon® LPC65, essentially consisting of partially hydrolyzed soybean lecithin.

In other particular such embodiments, the thickening/solidifying agent comprised within the formulation of the invention comprises a lecithin-like substance such as egg yolk.

In further particular such embodiments, the thickening/solidifying agent comprised within the formulation of the invention comprises a medium chain triglyceride, i.e., a triglyceride composed of a glycerol backbone and three fatty acids, wherein two or three of the fatty acids are medium chain fatty acids, i.e., fatty acids having an aliphatic chain of 6-12 carbon atoms, or a mixture thereof. Particular medium chain triglycerides that can be used include, without limiting, miglyol, and triglycerides of fractionated $C_8$-$C_{10}$ coconut oil fatty acids, e.g., miglyol 810.

In yet other particular such embodiments, the thickening/solidifying agent comprised within the formulation of the invention comprises a polysorbate, i.e., an oily liquid emulsifier derived from ethoxylated sorbitan esterified with fatty acids. Non-limiting examples of such polysorbates include polysorbate 20 (polyoxyethylene sorbitan monolaurate; Tween® 20), polysorbate 40 (polyoxyethylene sorbitan monopalmitate; Tween® 40), polysorbate 60 (polyoxyethylene sorbitan monostearate; Tween® 60), and polysorbate 80 (polyoxyethylene sorbitan monooleate; Tween® 80).

In still further particular such embodiments, the thickening/solidifying agent comprised within the formulation of the invention comprises sorbitol ((2S,3R,4R,5R)-hexane-1,2,3,4,5,6-hexol).

In certain embodiments, the antioxidant comprised within the formulation of the present invention is a thiol such as aurothioglucose, dihydrolipoic acid, propylthiouracil, thioredoxin, glutathione (GSH), L-cysteine, N-acetylcysteine (NAC), cystine, cystamine, and thiodipropionic acid; a sulphoximine such as buthionine-sulphoximine, homo-cysteine-sulphoximine, buthionine-sulphones, and penta-, hexa- or heptathionine-sulphoximine; a metal chelator such as a α-hydroxy-fatty acid, palmitic acid, phytic acid, lactoferrin, citric acid, lactic acid, malic acid, humic acid, bile acid, bile extracts, bilirubin, biliverdin, EDTA, $Na_2$-EDTA, $Na_2$-EDTA-Ca, EGTA, and DTPA; sodium bisulfite, and sodium metabisulfite; a vitamin such as vitamin E, ascorbic acid or ascorbic acid salts (Na-ascorbate, ascorbyl palmitate, Mg ascorbyl phosphate, and ascorbyl acetate); a phenol such as butylhydroxytoluene (BHT), butylhydroxyanisole, ubiquinol, nordihydroguaiaretic acid, and trihydroxybutyrophenone; a benzoate such as coniferyl benzoate; uric acid; mannose; propyl gallate; a selenium such as selenium-methionine; a stilbene such as stilbene oxide and trans-stilbene oxide; a carotenoid such as α-carotene, β-carotene, β-cryptoxanthin, lutein, zeaxanthin, astaxanthin, and lycopene; or a mixture thereof. A particular mixture of carotenoids that might be used is the commercially available product CarotenALL, Mixed Carotenoid Complex (Jarrow Formulas; http://www.iherb.com/Jarrow-Formulas-CarotenALL-Mixed-Carotenoid-Complex-60-Softels/153.

In particular embodiments, the antioxidant comprised within the formulation of the present invention is a phenol such as BHT, butylhydroxyanisole, ubiquinol, nordihydroguaiaretic acid, and trihydroxybutyrophenone; a carotenoid such as α-carotene, β-carotene, β-cryptoxanthin, lutein, zeaxanthin, astaxanthin, and lycopene; or a mixture thereof. More particular such embodiments are those wherein said antioxidant is BHT, carotenoid, or a mixture thereof.

In certain embodiments, the present invention provides a formulation as defined above, wherein the viscosity enhancing agent comprises a lecithin or a PEGylated derivative thereof, a lecithin-based product, or a povidone; and the antioxidant is BHT, butylhydroxyanisole, ubiquinol, nordihydroguaiaretic acid, trihydroxybutyrophenone, α-carotene, β-carotene, β-cryptoxanthin, lutein, zeaxanthin, astaxanthin, lycopene, or a mixture thereof. In some particular such embodiments, said lecithin is egg lecithin or soybean lecithin; said lecithin-based product is L-α-lecithin, granular (Acros Organics™), Phospholipon® 50, Phospholipon® 75, Phospholipon® 85G, Phospholipon® 90G, Phospholipon® 80H, Phospholipon® 90H, Phospholipon® E25, Phospholipon® E35, Phospholipon® E, Phospholipon® LPC20, Phospholipon® LPC25, or Phospholipon® LPC65; or said antioxidant is BHT, a carotenoid, or a mixture thereof. In other particular such embodiments, said viscosity enhancing agent comprises egg lecithin or soybean lecithin; and said antioxidant is BHT, α-carotene, β-carotene, β-cryptoxanthin, lutein, zeaxanthin, astaxanthin, lycopene, or a mixture thereof. Preferred such embodiments are those comprising egg lecithin or soybean lecithin as the viscosity enhancing agent, and BHT as the antioxidant. Formulations as defined hereinabove may comprise said viscosity enhancing agent and said antioxidant in a weight ratio that is in a range of about 100:1 to about 1:100, respectively, e.g., about 100:90, 100:80, 100:70, 100:60, 100:50, 100:40, 100:30, 100:20, 100:10 100:1, 1:100, 10:100, 20:100, 30:100, 40:100, 50:100, 60:100, 70:100, 80:100, or 90:100 (viscosity enhancing agent:antioxidant), respectively.

In certain embodiments, the active agent comprised within the formulation of the present invention, according to any one of the embodiments defined above, is 9CBC. In other embodiments, said active agent is a 9CBC derivative of the formula C as defined above. In particular such embodiments, the formulation disclosed herein comprises 9CBC, a soybean lecithin, and BHT, e.g., at a weight ratio of about 1:10:5, respectively.

As shown herein, 9CBC formulations according to the present invention are chemically stable, i.e., show almost no degradation at all of the active agent, for weeks, when stored under inert conditions, e.g., under argon or nitrogen atmosphere. Formulations according to the invention may thus be stored for relatively long durations of time, e.g., for at least 72 or 96 hours, i.e., 3 or 4 days, respectively, but preferably for 1, 2, 3, or 4 weeks; 1, 2, 3, 4, 5, or 6 months; or more, under inert conditions and optionally at a temperature below 0° C. (e.g., at about or less than −20° C.), without a substantial degradation of the active agent.

The pharmaceutical formulation of the present invention, as defined in any one of the embodiments above, is in the form of a solid, semi-solid, gel, or paste, and is thus preferably formulated for oral administration.

The pharmaceutical formulations provided by the present invention may be prepared by conventional techniques, e.g., as described in Remington: The Science and Practice of Pharmacy, 19$^{th}$ Ed., 1995. The formulations can be prepared, e.g., by uniformly and intimately bringing the active agent, i.e., 9CBC or a derivative thereof as defined herein, into association with a said viscosity enhancing agent and said at least one antioxidant; mixing said components; and then, if necessary, shaping the product into the desired formulation. The compositions may further include pharmaceutically acceptable carriers, fillers, diluents or adjuvants, and other inert ingredients and excipients. In one embodiment, the pharmaceutical formulation of the present invention is formulated as particles, e.g., micro particles or nanoparticles.

Pharmaceutical formulations according to the invention, for oral administration, may be formulated as tablets, troches, lozenges, hard or soft capsules, or syrups or elixirs. Such formulations may be prepared according to any method known in the art for the manufacture of pharmaceutical compositions and may further comprise one or more non-toxic pharmaceutical acceptable excipients, as well as agents selected from sweetening agents, flavoring agents, coloring agents and preserving agents in order to provide pharmaceutically elegant and palatable preparations. These excipients may be, e.g., inert diluents such as calcium carbonate, sodium carbonate, lactose, calcium phosphate, or sodium phosphate; granulating and disintegrating agents, e.g., corn starch or alginic acid; binding agents, e.g., starch, gelatin or acacia; and lubricating agents, e.g., magnesium stearate, stearic acid, or talc. Oral compositions in the form of tablets may be either uncoated or coated utilizing known techniques to delay disintegration and absorption in the gastrointestinal tract and thereby provide a sustained, i.e., extended or prolonged, action over a longer period. For example, a time delay material such as glyceryl monostearate or glyceryl distearate may be employed. They may also be coated using the techniques described in the U.S. Pat. Nos. 4,256,108, 4,166,452 and 4,265,874 to form osmotic therapeutic tablets for controlled release.

The pharmaceutical compositions of the invention may be formulated for controlled release of the active agent. Such compositions may be formulated as controlled-release matrix, e.g., as controlled-release matrix tablets in which the release of a soluble active agent is controlled by having the active diffuse through a gel formed after the swelling of a hydrophilic polymer brought into contact with dissolving liquid (in vitro) or gastro-intestinal fluid (in vivo). Many polymers have been described as capable of forming such gel, e.g., derivatives of cellulose, in particular the cellulose ethers such as hydroxypropyl cellulose, hydroxymethyl cellulose, methylcellulose or methyl hydroxypropyl cellulose, and among the different commercial grades of these ethers are those showing fairly high viscosity. In other configurations, the compositions comprise the active agent formulated for controlled release in microencapsulated dosage form, in which small droplets of the active agent are surrounded by a coating or a membrane to form particles in the range of a few micrometers to a few millimeters.

Another contemplated formulations are depot systems, based on biodegradable polymers, wherein as the polymer degrades, the active agent is slowly released. The most common class of biodegradable polymers is the hydrolytically labile polyesters prepared from lactic acid, glycolic acid, or combinations of these two molecules. Polymers prepared from these individual monomers include poly (D,L-lactide) (PLA), poly (glycolide) (PGA), and the copolymer poly (D,L-lactide-co-glycolide) (PLG).

The pharmaceutical formulations of the present invention are useful in treatment of any medical indication in which administration of 9CBC or a derivative thereof as defined herein is useful, e.g., neuro-retinal degeneration such as age related macular degeneration (AMD) and retinitis pigmentosa, and can be provided in a variety of dosages.

The dosage will depend on the state of the patient, i.e., the subject or individual treated, and will be determined as deemed appropriate by the practitioner. Depending on the active agent dosage, the formulations of the invention may be administered, e.g., daily, twice daily, thrice daily or four times daily, for various duration periods, e.g., days, weeks, months, years, or decades.

Unless otherwise indicated, all numbers expressing, e.g., the weight ratio between the active agent, viscosity enhancing agent, and antioxidant(s) composing the formulation of the present invention, as used in this specification, are to be understood as being modified in all instances by the term "about". Accordingly, unless indicated to the contrary, the numerical parameters set forth in this specification are approximations that may vary by up to plus or minus 10% depending upon the desired properties to be obtained by the present invention.

The invention will now be illustrated by the following non-limiting Examples.

EXAMPLES

Example 1. Synthesis of 9-cis-β-carotene

Materials and Methods

Ethyl 3,3-dimethylacrylate was purchased from Sigma Aldrich. β-cyclocitral was purchased from Alfa Aeser. All-trans retinal and triethyl 3-methyl-4-phosphono-2-butenoate were purchased from Toronto Research Chemicals (TRC). Triphenylphosphonium bromide was purchased from Acros Organics. α,α'-Azoisobutyronitrile (AIBN) was purchased from Molekula.

Experimental (General)

All reactions were carried out under argon/nitrogen atmosphere. The reactions (except for steps a and b in Scheme 1) were performed in the dark under red dim light.

As described herein and depicted in Scheme 1, 9-cis-β-carotene (9CBC) could be obtained by multi-step synthesis (8 steps). The building blocks for the synthesis of 9CBC are β-cyclocitral and all-trans retinal. 9CBC could be afforded by Wittig reaction of all-trans retinal and 9-cis retinyl triphenylphosphonium bromide salt (Goswami and Barua, 2003) which could be obtained from the building block, β-cyclocitral (Scheme 2).

Synthesis of ethyl 4-bromo-3-methylbut-2-enoate

As depicted in Scheme 2, N-bromosuccinimide (85 mmol 15.1 g) and a catalytic amount of AIBN (0.02 g) were added to a solution of ethyl 3,3-dimethylacrylate (78 mmol, 10 g) in carbon tetrachloride (128 mL) and the mixture was heated under reflux for 3 h. It was then cooled and filtered, and the precipitate was washed with chloroform. The combined organic phases were washed with saturated aqueous sodium sulfite and brine, dried (MgSO$_4$), and concentrated under reduced pressure to give the (E) and (Z)-4-bromo-3-methylbut-2-enoate. 4-Bromo-3-methylbut-2-enoate distilled under vacuum (3.6 mbar, 84-86° C.). HPLC analysis (C18-RP (5 µm) LiChrocart column): elution of CH$_3$CN/H$_2$O, 60:40 to 100:0, in 12 min (flow rate 1 mL/min). Retention time of ethyl 4-bromo-3-methylbut-2-enoate was 7 min (purity: 96%). The spectral data were consistent with literature (Mata and Thomas, 1995; Roder et al., 1980).

Reformatsky Reaction (Lactone Ring Formation) (U.S. Pat. No. 5,567,855) (Step a)

As depicted in Scheme 1, step a, in a 100 mL round-bottomed flask fitted with a reflux condenser, nitrogen inlet, and addition funnel was added 2.5 grams of zinc dust (38.28 mmol) and 4 mL of dry tetrahydrofuran. The β-cyclocitral (36.45 mmol, 5.88 mL) and ethyl 4-bromo-3-methylbut-2-enoate (36.51 mmol, 5.52 mL) were added to the addition funnel with 15 mL of dry tetrahydrofuran. The reactants were added dropwise following an initial addition of 1-2 mL to initiate the reaction. The rate of addition was adjusted to maintain a gentle reflux, with ca. 20-30 min for complete addition. The reaction solution was then heated to reflux for 30 minutes. After cooling to room temperature, 15 mL of saturated ammonium chloride solution was added and the solution stirred for 30 min. The reaction solution was worked up with addition of another 30 mL of saturated ammonium chloride solution to a 500 mL separatory funnel and dimethyl ether extraction (3×25 mL). The combined organic layers were washed with brine and dried over MgSO$_4$. Concentration in vacuo produced 8.95 g. The product was dissolved in hot hexane and allowed to recrystallize with cooling. The white solid was filtered and collected to yield 4.68 g lactone (55%). $^1$H-NMR (CDCl$_3$, 400 MHz); d (ppm) 5.82 (s, 1H), 4.96 (dd, 13.4, 4.4 1H), 2.88 (dd, 13.4, 18.5, 1H), 2.16 (dd, 18.5, 3.4, 1H), 1.98 (s, 3H), 1.96 (m, 1H), 1.75 (s, 3H), 1.57-1.65 (m, 2H), 1.42-1.50 (m, 2H), 1.09 (s, 3H), 0.97 (s, 3H). MS (ES$^+$) cacld for C$_{15}$H$_{22}$O$_2$ 234.3, found 235.3 (M-H$^+$). HPLC analysis (C18-RP (5 µm) LiChrocart column): elution of CH$_3$CN/H$_2$O, 60:40 to 100:0, in 12 min (flow rate 1 mL/min, λ=241 nm). Retention time of lactone was 9 min (purity: 96%).

Lactone Reduction (U.S. Pat. No. 5,567,855) (Step b)

As depicted in Scheme 1, step b, to 24 mL of tetrahydrofuran (THF) was added the lactone (14.08 mmol, 3.3 g). The resulting solution was cooled in a −78° C. bath and with constant stirring was aided DIBAL (18.4 mL, 1.0 M in CH$_2$Cl$_2$) dropwise, never allowing the solution to warm above −40° C. (2 h addition time). After 15-20 minutes the reaction was complete, as evidenced by TLC (Et$_2$O/Hexane; 40:60). To the cooled solution was added 500 mL of 10% H$_2$O/THF as a quenching solution. The solution was removed from the bath and allowed to warm to room temperature, while monitoring the rate of warming. After reaching ca. 10°–15° C., then was cooled by using of the cooling bath again. At this point, 2 g of Na$_2$SO$_4$ was added and the resulting suspension was stirred for 0.5 hours. The solution was filtered through a bed of celite, the bed washed with THF and the solution concentrated to yield oil with solid ppt (2.76 g). According to MS (ES$^+$) the aldehyde (step c) was formed with mass of 219.3 (M-H$^+$).

Ring Opening of Lactol (Aldehyde Formation) (U.S. Pat. No. 5,567,855) (Step c)

As depicted in Scheme 1, step c, In order to complete aldehyde formation step c was performed. To a solution of 23 mL of 1,2-dichloroethane was added 2.76 g of the lactol and 11.5 mL of 1N HCl solution. The two phase solution was heated to 40° C., and monitored by TLC. The solution turned orange after 30 min. The reaction was found to be complete after 12.5 hours (formed orange-red solution). The reaction was quenched by the separation of layers and 50 mL of saturated Na$_2$CO$_3$ carefully added to the organic layer with stirring. The aqueous layer was washed with two portions of dichloromethane and the collective organic layers washed once with brine. The organic solution was then dried over K$_2$CO$_3$ (anhydrous) and concentrated in vacuo to afford a red-orange oil to afford 2.274 grams (60% for steps b and c). $^1$H-NMR (CDCl$_3$, 400 MHz): d (ppm) 10.16 (d, 8.0, 1H), 7.08 (d, 16.0, 1H), 6.63 (d, 15.0, 1H), 5.86 (d, 8.0, 1H), 2.12 (s, 3H), 2.05 (t, 6.0, 2H), 1.75 (s, 3H), 1.57-1.75 (m, 2H), 1.40-1.53 (m, 2H), 1.05 (s, 6H). MS (ES$^+$) cacld for C$_{15}$H$_{22}$O 218.3, found 219.3 (M-H$^+$). HPLC analysis (C18-RP (5 µm) LiChrocart column): elution of CH$_3$CN/H$_2$O, 60:40 to 100:0, in 12 min and then 100% $CH_3CN$ for 5 min (flow rate 1 mL/min, $\lambda$=396 nm). Retention time of lactone was 13 min (purity: 90%).

Horner-Emmons Reaction (9-Cis Retinyl Ester Formation) (U.S. Pat. No. 5,567,855; Bennani and Boehm, 1995) (Step d)

As depicted in Scheme 1, step d, a solution of triethyl 3-methyl-4-phosphono-2-butenoate (14.42 mmol, 3.51 mL) in anhydrous THF (21.7 mL) was cooled to 0° C. and treated with anhydrous DMPU (29.7 mmol, 3.57 mL) and n-BuLi in hexanes (6.08 mL of 2.5 M solution, 15.21 mmol). The mixture was stirred at this temperature for 20 min and then cooled to −78° C. A solution of aldehyde (7.93 mmol 1.73 g) in THF (21.7 mL) was slowly added and the reaction mixture stirred at −78° C. for an additional 60 min. The mixture was allowed to warm to 0° C. to effect completion of the reaction (TLC, 8:2 hexane:diethyl ether). A saturated solution of ammonium chloride (15 mL) was added and the mixture extracted with EtOAc (3×20 mL). The organic layer was washed with water (2×10 mL) and brine (20 mL), dried over $MgSO_4$, and concentrated to give 6.33 g red oil. The residue was purified on a short SilicaGel column (95:5 hexane: diethyl ether) to give 1.85 g (71% yield) of the desired ester. 9-cis retinyl ester from its trans isomer by preparative HPLC (cosmosil cholester packed column 20.0 mm I.D×250 mm) using elution of $CH_3OH/H2O$, 90:10 for 4 min then, 90:10 to 95:05 for 4 min, and then 95:05 for 17 min (flow rate 25 mL/min, $\lambda$=402 nm). Retention time was 13.7 min.

Analytic HPLC analysis (cosmosil cholester packed column 4.6 mm I.D×250 mm): isocratic elution of $CH_3OH/H_2O$ 95:05, in 12 min (flow rate 2 mL/min). Retention time was 8 min (99.6% purity). $^1$H-NMR ($CDCl_3$, 400 MHz); d (ppm) 7.08 (dd, 15, 11.3, 1H), 6.65 (d, 16, 1H), 6.29 (d, 15, 1H), 6.22 (d, 15, 1H), 6.05 (d, 11.9, 1H), 5.77 (s, 1H), 4.17 (q, 2H), 2.34 (s, 3H), 2.05 (t, 2H), 2.00 (m, 3H). 1.75 (s, 3H), 1.64 (m, 2H), 1.49 (m, 2H), 1.28 (t, 3H), 104 (s, 6H). MS ($ES^+$) cacld for $C_{22}H_{32}O_2$ 328.5, found 329.4 ($M-H^+$). 2D COSY NMR experiment (700 MHz) proved that 9-cis retinyl ester was obtained.

Ester Reduction (9-cis-retinol Formation) (Step e) (Alvarez et al., 2001)

As depicted in Scheme 1, step e, to a solution of ethyl 9-cis retinyl ester (1.674 mmol 0.55 g) in THF (5 mL) at −78° C., was added DIBAL-H (7 mL, 1M in hexane, 7 mmol) and the resulting suspension was stirred for 1 h at −78° C. After careful addition of 10% aqueous $NH_4Cl$, the mixture was extracted with ethyl ether (3×10 mL). The combined organic layers were dried over $MgSO_4$ and concentrated in vacuo. The residue was used in the next step without further purification. Analytic HPLC analysis (cosmosil cholester packed column 4.6 mm I.D×250 mm): Elution of $CH_3CN/H_2O$, 65:35 to 80:20, in 20 min, and then 100% $CH_3CN$ for 8 min (flow rate 2 mL/min, $\lambda$=370 nm). $^1$H-NMR (400 MHz) showed typical peaks of the alcohol group at 4.25 ppm (2H) and 3.71 ppm (OH, broad peak). Retention time was 13.4 min (87% purity). MS ($ES^+$) cacld for $C_{20}H_{30}O$ 286.45, found 269.3 (M-(OH)).

9-cis-retinylphosphonium Salt Formation 1 (Step f)

As depicted in Scheme 1, step f, to a solution of 9-cis retinol (0.77 mmol, 220 mg) in dry MeOH (1 ml), triphenylphosphine hydrobromide (0.88 mmol 320 mg) in MeOH was added dropwise with stirring. The mixture was stirred at room temperature under argon. After 1 h, the solvent was evaporated in a rotary evaporator and the light orange residue was washed with 10 ml portions of hexane 5-6 times to remove side products. Analytic HPLC analysis (cosmosil cholester packed column 4.6 mm I.D×250 mm): Elution of $CH_3CN$ (0.1% TFA)/$H_2O$ (0.1% TFA), 65:35 for 4 min, then from 65:35 to 75:25 for 8 min, and finally isocratic elution 75:25 $CH_3CN$ (0.1% TFA)/$H_2O$ (0.1% TFA) for 4 min (flow rate 2 mL/min, $\lambda$=370 nm). Retention time was 10.8 min (72% purity). MS ($ES^+$) cacld for $C_{38}H_{44}P^+$ 531.3, found 531.4 (M), 532.3 ($M-H^+$).

Wittig Reaction 9CBC Formation (Step g) (Goswami and Barua, 2003)

As depicted in Scheme 1, step g, to a stirred solution of 86 mg of 9-cis retinyl triphenylphosphonium bromide (0.14 mmol) in 2 ml of dry ethanol at 70° C., all-trans retinal (19.7 mg, 0.069 mmol) in 17 ml of dry ethanol was added dropwise. KOH (0.43 g) dissolved in dry ethanol (5 ml) was added slowly to the mixture, and the solution was stirred at 70° C. for 15 min and then at room temperature for 2 h. The reaction was monitored by TLC (8:2 hexane:ethyl acetate). When no more carotene formation was noted after 2 h, water (10 ml) was added to the reaction mixture and the product was extracted with portions of diethyl ether. The organic phase was removed under vacuum. MS (APPI) of crude cacld for $C_{40}H_{56}$ 536.4, found 536.4 (M), 537.4 ($M-H^+$). HPLC analysis of the crude (cosmosil cholester packed column 4.6 mm I.D×250 mm) isocratic elution of $CH_3OH/CHCl_3$, 80:20 for 16 min (flow rate 2 mL/min, $\lambda$=447 nm). Retention time was 11 min. (87% purity, FIG. 1). 9CBC purified by preparative HPLC (Cholester packed column) using elution of $CH_3OH:CHCl_3$, 85:15 for 5 min, then 85:15 to 80:20 for 5 min and then isocratic elution of 80:20 for 20 min (flow rate 25 mL/min, $\lambda$=447 nm). Retention time was 16 min. MS (APPI) of crude cacld for $C_{40}H_{56}$ 536.4, found 536.4 (M), 537.4 ($M-H^+$).

It is also possible to substitute $CHCl_3$ with methylene chloride for preventing possible damage during separation. Likewise, the final separation can be done with Methyl tert-butyl ether and acetonitrile, instead of the solvents mentioned above.

Example 2. Stable Formulations of 9-cis-β-carotene

Purified 9CBC was found to be unstable under vacuum or nitrogen flushing. In this study, various 9CBC formulations comprising a natural or synthetic commercially available antioxidant(s), a viscosity enhancing agent, or both, were prepared, and the chemical stability of some of these formulations were tested.

The specific formulations prepared were:

1. Lecithin+antioxidants mix [a pellet content from the commercially available product CarotenALL, Mixed Carotenoid Complex (Jarrow Formulas)]+9CBC (10:5:1 w/w/w)
2. Lecithin+BHT+9CBC (10:5:1 w/w/w)
3. Miglyol 810+antioxidant mix+9CBC (100:5:1)
4. Miglyol 810+BHT+9CBC (100:5:1)
5. Tween 40+9CBC
6. Tween 20+antioxidant mix+9CBC
7. Tween 40+antioxidant mix+9CBC Table 1 shows spectral tests confirming the stability of 9CBC in the formulations tested within the specified time period. As clearly indicated, lecithin as an excipient and binder plays a crucial role in stabilizing 9-CBC. Interestingly, although a formulation comprising an antioxidant only as the anti-degradative measure (as disclosed in U.S. Pat. No. 5,612,485) has somewhat of a positive effect during the first 14 days, said formulation has rapidly degraded during the next days, wherein the measurable 9-CBC by day 22 was almost as low as in the blank formulation. In fact, as shown in Table 1, the amount of 9CBC in said antioxidant-based formulation was significantly lower than that in the formulation that further contained a viscosity enhancing agent (lecithin), already after 14 days, suggesting that 9CBC degradation starts during the first 14 days and intensifies later. In sharp contrast, the measurable amount of 9CBC in the formulation containing both antioxidant and a viscosity enhancing agent was almost 100% compared to the initial amount, indicating the stability of said formulation.

TABLE 1

Results of spectral tests of the various formulations tested

| Tested medium | Absorption at 447/450 nm 14 days | Absorption at 447/450 nm 22 days |
| --- | --- | --- |
| Diethyl ether | 0 | 0 |
| Diethyl ether + lecithin + BHT | 0.71/0.69 | 0.73/0.70 |
| Diethyl ether + BHT + 9CBC | 2.11/2.08 | 1.05/0.96 |
| Diethyl ether + lecithin + BHT + 9CBC | 2.43/2.32 | 2.42/2.30 |

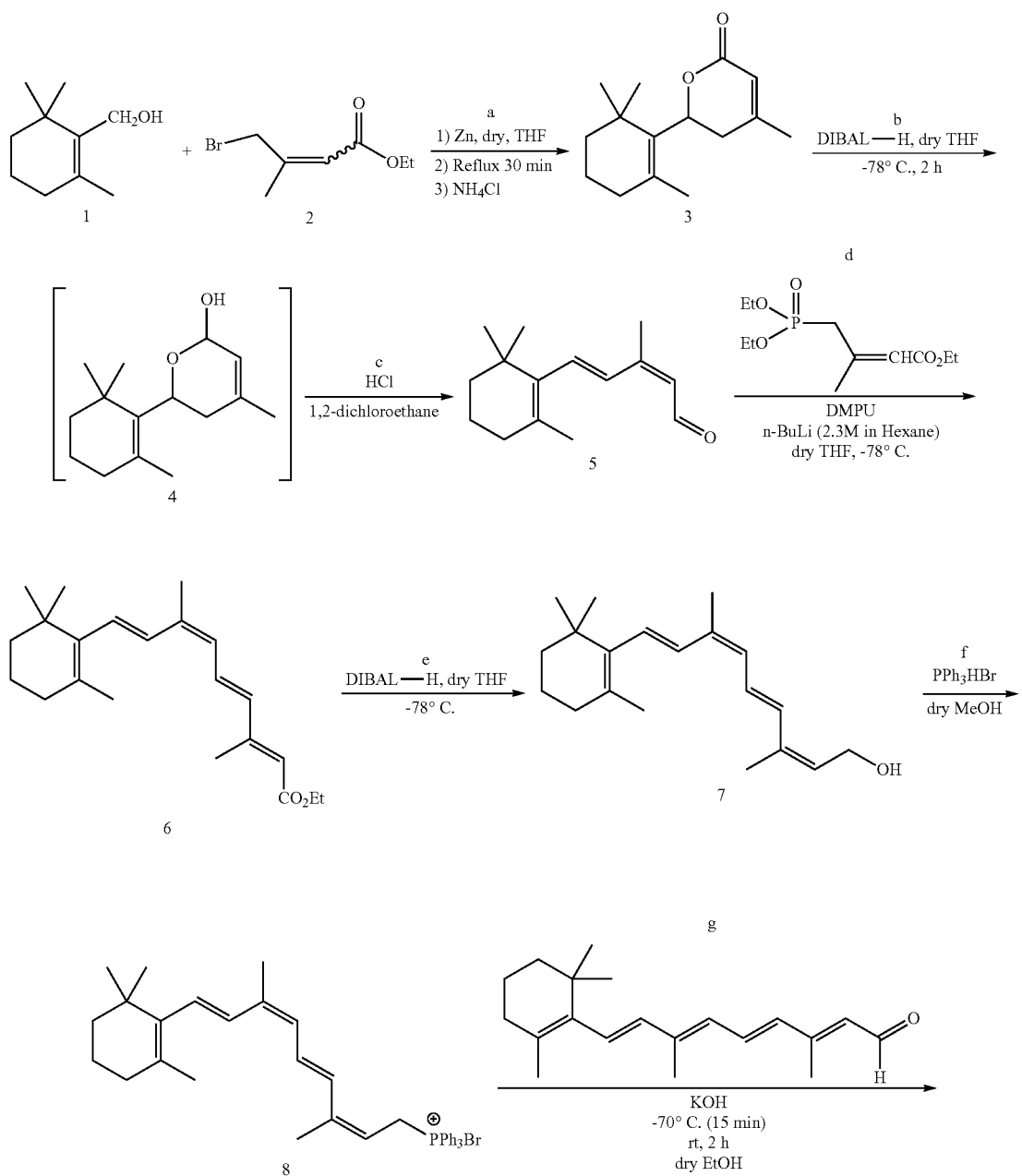

Scheme 1. Synthesis of 9-cis-β-carotene

-continued
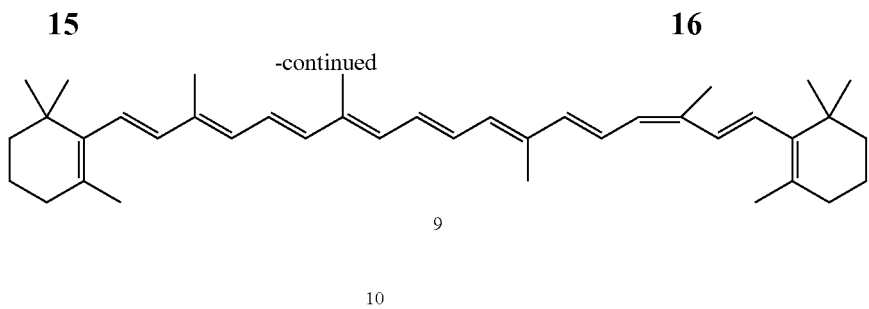
9
Scheme 2. Synthesis of ethyl 4-bromo-3-methylbut-2-enoate
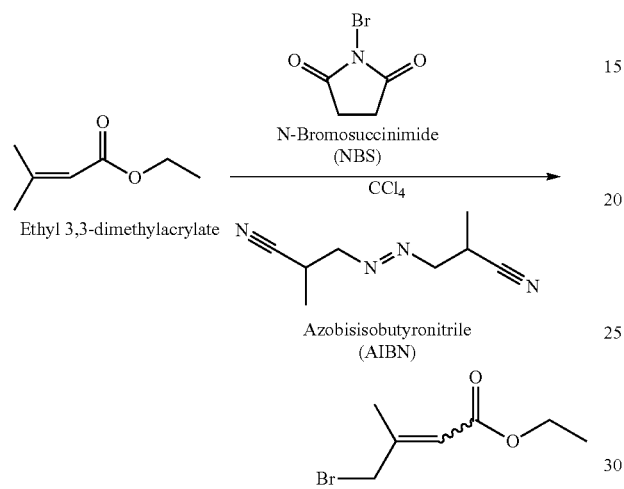
Scheme 3. Retrosynthesis of 9-cis-β-carotene
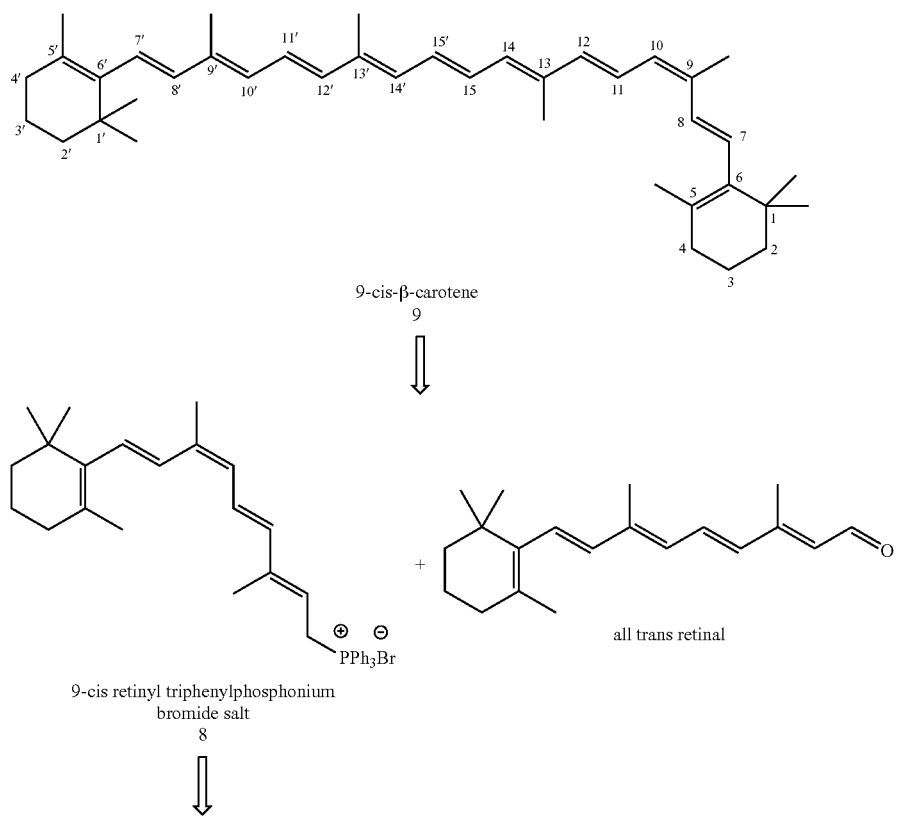

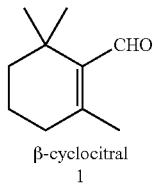

β-cyclocitral
1

REFERENCES

Alvarez, R.; Dominguez, B.; de Lera, A. R., *Synth. Commun.* 2001, 31, 2083-2087

Alvarez, R.; Domínguez, M.; Pazos, Y.; Sussman, F.; de Lera, A. R., *Chem. Eur. J.* 2003, 9, 5821-5831

Bennani, Y. L.; Boehm, M. F. *J. Org. Chem.* 1995, 60, 1195-1200

Goswami, B. C.; Barua, A. B., *J. Labelled Comp. Radiopharm.* 2003, 46, 843-849

López, S.; Montenegro, J.; Saá, C., *J. Org. Chem.* 2007, 72, 9572-9581

Mata, E. G.; Thomas, E. J., *J. Chem. Soc.-Perkin Trans.* 1 1995, 785-799

Roder, E.; Wiedenfeld, H.; Frisse, M., *Arch. Pharm.* 1980, 313, 803-806

The invention claimed is:

1. A method for the synthesis of 9-cis β-carotene (9CBC) or a derivative thereof, said method comprising:
   (i) reducing 4-methyl-6-(2,6,6-trimethylcyclohex-1-en-1-yl)-5,6-dihydro-2H-pyran-2-one, herein identified compound 3, and opening the ring of the lactol obtained with complete retention of the double bond configuration, to thereby obtain (2Z,4E)-3-methyl-5-(2,6,6-trimethylcyclohex-1-en-1-yl)penta-2,4-dienal, herein identified compound 5;
   (ii) subjecting the (2Z,4E)-3-methyl-5-(2,6,6-trimethylcyclohex-1-en-1-yl)penta-2,4-dienal to Horner-Emmons reaction to obtain a 9-cis retinyl ester, herein identified compound 6;
   (iii) reducing the 9-cis retinyl ester to obtain 9-cis retinol, herein identified compound 7; and
   (iv) converting the 9-cis retinol to its triphenylphosphonium salt, herein identified compound 8, and subjecting said triphenylphosphonium salt to Wittig reaction with a compound of the formula A:

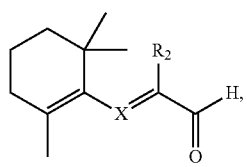

A wherein $R_2$ is H or methyl; X is

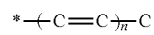

optionally substituted with one or more methyl groups; n is an integer of 0-16; and the asterisk represents the point of attachment to the cyclohexene ring, in the presence of a strong base, to thereby obtain said 9CBC or derivative thereof.

2. The method of claim 1, wherein:
   (i) the reduction in step (i) is carried out with diisobutylaluminum hydride (DIBAL-H); or
   (ii) opening the ring of the lactol in step (i) is carried out in the presence of a strong acid; or
   (iii) the Horner-Emmons reaction in step (ii) is carried out with triethyl 3-methyl-4-phosphono-2-butenoate to obtain 9-cis retinyl ethyl ester; or
   (iv) converting the 9-cis retinol to its triphenylphosphonium salt in step (iv) is carried out with triphenylphosphine; or
   (v) said compound of the formula A is all-trans retinal, to obtain 9CBC.

3. The method of claim 1, wherein said 4-methyl-6-(2,6,6-trimethylcyclohex-1-en-1-yl)-5,6-dihydro-2H-pyran-2-one is synthesized by reacting β-cyclocitral, herein identified compound 1, with a compound of the formula B:

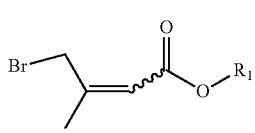

B wherein $R_1$ is $(C_1-C_8)$alkyl or $(C_6-C_{10})$aryl, in the presence of metallic Zn, in a Reformatsky reaction.

4. The method of claim 3, wherein said β-cyclocitral is reacted with a compound of the formula B wherein $R_1$ is ethyl.

* * * * *